(12) United States Patent
Nishino et al.

(10) Patent No.: US 7,745,649 B2
(45) Date of Patent: Jun. 29, 2010

(54) PROCESSES FOR PREPARING TETRAHYDROPYRAN-4-ONE AND PYRAN-4-ONE

(75) Inventors: Shigeyoshi Nishino, Ube (JP); Kenji Hirotsu, Ube (JP); Hidetaka Shima, Ube (JP); Shinobu Suzuki, Ube (JP)

(73) Assignee: UBE Industries, Ltd., Ube-shi (JP)

( * ) Notice: Subject to any disclaimer, the term of this patent is extended or adjusted under 35 U.S.C. 154(b) by 981 days.

(21) Appl. No.: 10/583,562

(22) PCT Filed: Dec. 17, 2004

(86) PCT No.: PCT/JP2004/018949

§ 371 (c)(1),
(2), (4) Date: Jun. 19, 2006

(87) PCT Pub. No.: WO2005/061479

PCT Pub. Date: Jul. 7, 2005

(65) Prior Publication Data

US 2007/0078272 A1    Apr. 5, 2007

(30) Foreign Application Priority Data

| Dec. 19, 2003 | (JP) | ............................. | 2003-422053 |
| Apr. 5, 2004 | (JP) | ............................. | 2004-110673 |
| Apr. 5, 2004 | (JP) | ............................. | 2004-110674 |
| Apr. 14, 2004 | (JP) | ............................. | 2004-118686 |
| May 10, 2004 | (JP) | ............................. | 2004-140152 |
| Jul. 5, 2004 | (JP) | ............................. | 2004-198148 |

(51) Int. Cl.
*C07D 309/30* (2006.01)
(52) U.S. Cl. .................................................. 549/416
(58) Field of Classification Search .................. 549/416
See application file for complete search history.

(56) References Cited

U.S. PATENT DOCUMENTS 4,837,345 A    6/1989  Numata et al.

FOREIGN PATENT DOCUMENTS

| GB | 1315630 A | 5/1973 |
| JP | 47-29512 | 8/1972 |
| JP | 63-170372 A | 7/1988 |
| JP | 7-145162 A | 6/1995 |

| JP | 10-45660 A | 2/1998 |

OTHER PUBLICATIONS

Mazzieri et al, Reaction Kinetics Catalysis Letters, vol. 81(1), p. 107-112 (2004).*
Cornubert et al, Bull. de la Societe chimique de France, p. 46-50 (1950) -English translation.*
Cornubert, R. et al., Bulletin de la Societe chimique de France, 1950, pp. 36-40.
Sorkin, E. et al., Helvetica Chimica Acta, 1948, vol. 31, pp. 65-75.
Yoshiro Ogata, "Yuki Kagobutsu no Sanka to Kangen", 1964 Nen, Nankodo Co., Ltd., pp. 528-532, 536-540.
Chinese Office Action issued in Chinese Application No. 2004800380429 (Dated May 9, 2008).
Chinese Office Action issued in Chinese Application No. 2004800380429 (Dated May 9, 2009).
Supplementary European Search Report issued in European Application No. 04807306 (Dated Jun. 19, 2009).

* cited by examiner

*Primary Examiner*—Bernard Dentz
(74) *Attorney, Agent, or Firm*—Birch, Stewart, Kolasch & Birch, LLP

(57) ABSTRACT

The present invention relates to a process for preparing tetrahydropyran-4-one represented by the formula (1):

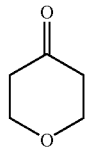

(1)

which comprises reacting at least one kind of dihydropyran-4-one and pyran-4-one represented by the formula (2):

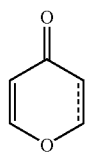

(2)

wherein ----- represents a single bond or a double bond, and hydrogen
(a) in the presence of a metal catalyst, in a mixed solvent of an aprotic solvent and an alcohol solvent, or
(b) in the presence of an anhydrous metal catalyst in which a hydrated metal catalyst is subjected to dehydration treatment, in a hydrophobic organic solvent.

23 Claims, No Drawings

PROCESSES FOR PREPARING TETRAHYDROPYRAN-4-ONE AND PYRAN-4-ONE

TECHNICAL FIELD

The present invention relates to processes for preparing pyran-4-one and tetrahydropyran-4-one. Pyran-4-one and tetrahydropyran-4-one are useful compounds as starting materials or synthetic intermediates of medicine, agricultural chemicals, etc.

BACKGROUND ART

Heretofore, as a process for preparing pyran-4-one, there have been known, for example, a method in which 4-methoxy-3-buten-2-one and methyl formate are reacted in ether in the presence of sodium methoxide to precipitate a sodium salt of a formyl derivative, then, a methanol solution of hydrogen chloride is reacted thereto, neutralized and distilled under reduced pressure to give a mixture containing 1,5,5-trimethoxy-1-penten-3-one as a main component, further, the mixture is allowed to stand in conc. hydrochloric acid overnight, then neutralized and extracted to prepare pyran-4-one (for example, see Patent literature 1). However, according to this method, a sodium salt of a formyl derivative which is an intermediate must be once precipitated, and, a methanol solution of hydrogen chloride which is difficult to handling must be used, a reaction operation is complicated and a reaction time is extremely long, so that it is not advantageous as an industrial process for preparing pyran-4-one.

Moreover, as a process for preparing tetrahydropyran-4-one from pyran-4-one, there has been disclosed, for example, a method in which pyran-4-one and hydrogen are reacted in the presence of Raney nickel, under normal pressure in ethanol at room temperature for 3 hours to prepare tetrahydropyran-4-one with yield of 58% (for example, see Non-Patent literature 1) or a method in which pyran-4-one and hydrogen are reacted in the presence of palladium/scandium carbonate under pressure in methanol at 20° C. for 30 minutes to prepare tetrahydropyran-4-one with yield of 75% (for example, see Non-Patent literature 2).

However, in the processes for preparing pyran-4-one, there are problems that a sodium salt of a formyl derivative which is an intermediate must be once precipitated, and, a methanol solution of hydrogen chloride which is difficult to handling must be used, a reaction operation is complicated and a reaction time is extremely long, and in a method for preparing tetrahydropyran-4-one from pyran-4-one, minute operation such as adjustment of catalyst activity shall be carried out to improve yield of the objective compound, so that it is not advantageous as an industrial process for preparing tetrahydropyran-4-one.

[Patent literature 1] Japanese Patent Publication No. Sho. 47-29512

[Non-Patent literature 1] Bulletin de la Societe Chimique de France, 1959, 36.

[Non-Patent literature 2] Helv. Chim. Acta., 31, 65(1948)

DISCLOSURE OF THE INVENTION

Problems to be Solved by the Invention

An object of the present invention is to overcome the above-mentioned problems, and to provide a process for preparing pyran-4-one, which is preferable for industry from inexpensive starting materials with a simple and easy process in high yield.

Another object of the present invention is to overcome the above-mentioned problems, and to provide a process for preparing tetrahydropyran-4-one, which is preferable for an industrially suitable process for preparing from pyran-4-one with a simple and easy process in high yield.

MEANS TO SOLVE THE PROBLEMS

The first invention is to provide a process for preparing tetrahydropyran-4-one represented by the formula:

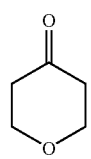

(1)

which comprises reacting at least one of dihydropyran-4-one and pyran-4-one represented by the formula (2):

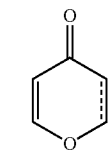

(2)

wherein ----- represents a single bond or a double bond, and hydrogen (a) in the presence of a metal catalyst, in a mixed solvent of an aprotic solvent and an alcohol solvent, or (b) in the presence of an anhydrous metal catalyst in which a hydrated metal catalyst is subjected to dehydration treatment, in a hydrophobic organic solvent.

The second invention relates to a process for preparing tetrahydropyran-4-one which comprises two steps of (A) cyclization step in which 1,1-dialkoxybutan-3-one represented by the formula (7):

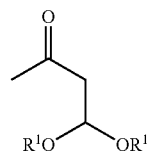

(7)

wherein $R^1$ represents an alkyl group, and two $R^1$s may be bonded to form a ring, and a formic acid ester represented by the formula (5):

$HCO_2R^2$ (5)

wherein $R^2$ represents an alkyl group, are reacted in an organic solvent in the presence of a base, to prepare a salt of 5,5-dialkoxy-3-oxopentanal represented by the formula (3):

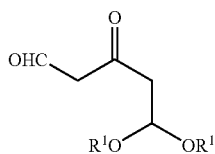

(3)

wherein $R^1$ has the same meaning as defined above, or a salt of an equivalent thereof, and reacting the salt with an acid to prepare crude product containing pyran-4-one represented by the formula (2'):

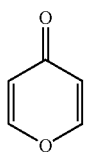

(2')

as a main component, then, (B) reduction step in which the crude product containing the pyran-4-one as a main component and hydrogen are reacted in the presence of a metal catalyst, (a) in a mixed solvent of an aprotic solvent and an alcohol solvent, or (b) in the presence of an anhydrous metal catalyst in which a hydrated metal catalyst is subjected to dehydration treatment, in a hydrophobic solvent, to prepare tetrahydropyran-4-one represented by the formula (1):

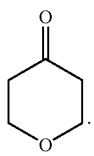

(1)

The third invention relates to a process for preparing pyran-4-one represented by the formula (2'):

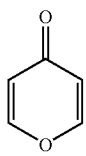

(2')

which comprises reacting a salt of 5,5-dialkoxy-3-oxopentanal represented by the formula (3):

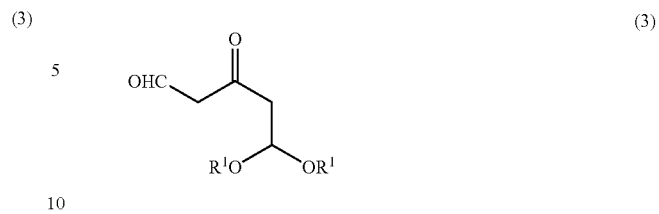

(3)

wherein $R^1$ has the same meaning as defined above, or a salt of the equivalent thereof with an acid.

The fourth invention relates to a process for preparing a salt of 5,5-dialkoxy-3-oxopentanal represented by the formula (3):

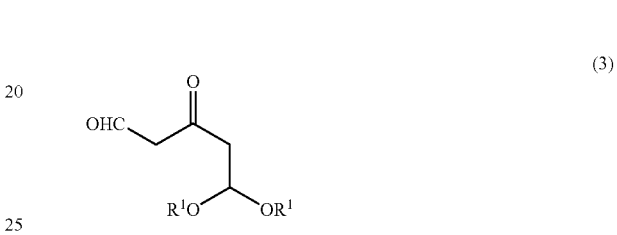

(3)

wherein $R^1$ has the same meaning as defined above, or a salt of the equivalent thereof which comprises reacting 1,1-dialkoxybutan-3-one represented by the formula (7):

(7)

wherein $R^1$ has the same meaning as defined above, and a formic acid ester represented by the formula (5):

$$HCO_2R^2 \quad (5)$$

wherein $R^2$ has the same meaning as defined above, in the presence of a base in an organic solvent.

The fifth invention relates to a process for preparing pyran-4-one represented by the formula (2'):

(2')

which comprises subjecting 1,1,5,5-tetraalkoxypentan-3-one represented by the formula (6):

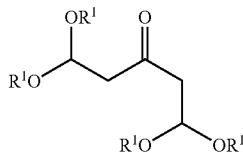

wherein R¹ has the same meaning as defined above, to cyclization in the presence of an acid.

The sixth invention relates to a process for preparing dihydropyran-4-one represented by the formula (2"):

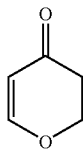

which comprises reacting pyran-4-one represented by the formula (2'):

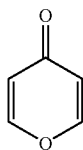

among the compounds represented by the formula (2) and hydrogen in the presence of a metal catalyst, in a mixed solvent of an aprotic solvent and an alcohol solvent.

The seventh invention relates to a sodium salt of 5,5-dialkoxy-3-oxopentanal represented by the formula (3):

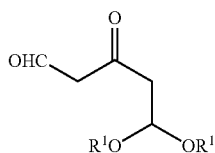

wherein R¹ has the same meaning as defined above, or a sodium salt of an equivalent thereof.

EFFECTS OF THE INVENTION

According to the present invention, an industrially suitable process for preparing tetrahydropyran-4-one which can obtain tetrahydropyran-4-one from pyran-4-one in high yield and by a simple and easy process can be provided.

Also, according to the present invention, an industrially suitable process for preparing pyran-4-one which can obtain pyran-4-one from inexpensive starting materials in high yield and by a simple and easy process can be provided.

BEST MODE FOR CARRYING OUT THE INVENTION

The first invention relates to a process for preparing tetrahydropyran-4-one represented by the formula (1):

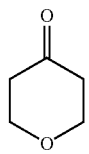

which comprises reacting at least one kind of dihydropyran-4-one and pyran-4-one represented by the formula (2):

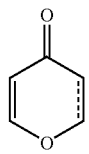

wherein ----- represents a single bond or a double bond, and hydrogen (a) in the presence of a metal catalyst, in a mixed solvent of an aprotic solvent and an alcohol solvent, or (b) in the presence of an anhydrous metal catalyst in which a hydrated metal catalyst is subjected to dehydration treatment, hydrophobic organic solvent.

As the metal catalyst of (a) to be used in the reaction of the present invention, there may be mentioned those which contain at least one metal atom selected from the group consisting of palladium, platinum and nickel, more specifically, there may be mentioned, for example, palladium/carbon, palladium/barium sulfate, palladium hydroxide/platinum, platinum/carbon, platinum sulfate/carbon, palladium-platinum/carbon, platinum oxide, Raney nickel, etc. Incidentally, these metal catalysts may be used alone or in combination of two or more in admixture.

An amount of the above-mentioned metal catalyst to be used is preferably 0.0001 to 5 mol, more preferably 0.0002 to 1 mol, further preferably 0.0005 to 0.5 mol, most preferably 0.001 to 0.1 mol based on 1 mol of the pyran-4-one and/or dihydropyran-4-one in terms of metal atom.

An amount of the hydrogen to be used in the reaction (a) of the first invention is preferably 0.5 to 20 mol, more preferably 1.1 to 10 mol, further preferably 2.1 to 5 mol based on 1 mol of the pyran-4-one and/or dihydropyran-4-one.

The mixed solvent of (a) to be used in the reaction of the first invention is a mixed solvent of an aprotic solvent and an alcohol solvent, and the alcohol solvent in the mixed solvent is preferably 1 to 95% by volume, further preferably 5 to 90% by volume. Also, an amount of the above-mentioned mixed solvent to be used may be optionally adjusted depending on a degree of uniformity or condition of stirring of the reaction solution, and is preferably 0.5 to 50 g, further preferably 1 to 20 g based on 1 g of the pyran-4-one and/or dihydropyran-4-one.

As the above-mentioned aprotic solvent, there may be mentioned an aliphatic hydrocarbon such as pentane, hexane, heptane, cyclohexane, etc.; a halogenated aliphatic hydrocarbon such as methylene chloride, dichloroethane, etc.; an aromatic hydrocarbon such as benzene, toluene, xylene, etc.; a halogenated aromatic hydrocarbon such as chlorobenzene, dichlorobenzene, etc., a carboxylic acid ester such as methyl acetate, ethyl acetate, etc.; an ether such as diethyl ether, tetrahydrofuran, dimethoxyethane, etc., preferably an aromatic hydrocarbon, further preferably toluene, xylene may be used. Incidentally, these aprotic solvents may be used alone or in combination of two or more in admixture.

As the above-mentioned alcohol solvent, there may be mentioned methanol, ethanol, n-propyl alcohol, isopropyl alcohol, and t-butyl alcohol. Incidentally, these alcohol solvents may be used alone or in combination of two or more in admixture.

The reaction of the first invention can be carried out, for example, in a hydrogen gas atmosphere, pyran-4-one and/or dihydropyran-4-one, a metal catalyst, an aprotic solvent and an alcohol solvent are mixed and reacted with stirring, and the like. The reaction temperature at that time is preferably 0 to 100° C., further preferably 5 to 60° C., and the reaction pressure is preferably 0.1 to 10 MPa, further preferably 0.1 to 1 MPa.

As the hydrated metal catalyst of (b) to be used in the reaction of the first invention, it is those containing at least one metal atom selected from the group consisting of palladium, platinum and nickel which are the same as the above-mentioned (a), and more specifically, there may be mentioned, for example, palladium/carbon, palladium/barium sulfate, palladium hydroxide/platinum, platinum/carbon, platinum sulfate/carbon, palladium-platinum/carbon, platinum oxide, Raney nickel, etc. Incidentally, these hydrated metal catalysts may be used alone or in combination of two or more in admixture, and they may be in a state in which it is suspended in water in the point of safety.

An amount of the above-mentioned hydrated metal catalyst to be used is preferably 0.0001 to 5 mol, further preferably 0.0002 to 1 mol based on 1 mol of the pyran-4-one and/or dihydropyran-4-one in terms of the metal atom.

An amount of the hydrogen to be used in the reaction (b) of the first invention is preferably 0.5 to 20 mol, more preferably 1.1 to 10 mol, further preferably 1.1 to 5 mol based on 1 mol of the pyran-4-one and/or dihydropyran-4-one.

As the hydrophobic organic solvent of (b) to be used in the reaction of the first invention, there may be mentioned, for example, an aliphatic hydrocarbon such as pentane, hexane, heptane, cyclohexane, etc.; a halogenated aliphatic hydrocarbon such as methylene chloride, dichloroethane, etc.; an aromatic hydrocarbon such as benzene, toluene, xylene, etc.; a halogenated aromatic hydrocarbon such as chlorobenzene, dichlorobenzene, etc.; a carboxylic acid ester such as methyl acetate, ethyl acetate, butyl acetate, etc.; an ether such as diethyl ether, etc., preferably an aliphatic hydrocarbon and/or an aromatic hydrocarbon is/are used. Incidentally, these hydrophobic organic solvents may be used alone or in combination of two or more in admixture.

An amount of the above-mentioned hydrophobic organic solvent to be used may be optionally adjusted depending on a degree of uniformity or condition of stirring of the reaction solution, and is preferably 0.5 to 50 g, more preferably 1 to 20 g, further preferably 1 to 10 g based on 1 g of the pyran-4-one and/or dihydropyran-4-one.

The dehydration treatment in the present invention is not specifically limited so long as it is a method in which a hydrated metal catalyst is made an anhydrous metal catalyst, and there may be suitably used a method, for example, in which a hydrated metal catalyst and an organic solvent which can be subjected to azeotropic distillation with water are mixed, and water is removed under reflux, etc., to remove water from the hydrated metal catalyst.

As the above-mentioned organic solvent which can be subjected to azeotropic distillation with water, there may be mentioned, for example, an aliphatic hydrocarbon such as pentane, hexane, heptane, cyclohexane, etc.; a halogenated aliphatic hydrocarbon such as methylene chloride, dichloroethane, etc.; an aromatic hydrocarbon such as benzene, toluene, xylene, etc.; a halogenated aromatic hydrocarbon such as chlorobenzene, dichlorobenzene, etc.; a carboxylic acid ester such as methyl acetate, ethyl acetate, butyl acetate, etc.; an ether such as diethyl ether, tetrahydrofuran, dimethoxyethane, etc., preferably an aliphatic hydrocarbon, an aromatic hydrocarbon, or an ether may be used. Incidentally, these organic solvents may be used alone or in combination of two or more in admixture.

An amount of the above-mentioned organic solvent which can be subjected to azeotropic distillation with water to be used is preferably 0.5 to 50 g, further preferably 1 to 20 g based on 1 g of the pyran-4-one and/or dihydropyran-4-one.

Incidentally, the above-mentioned organic solvent which can be subjected to azeotropic distillation with water and the hydrophobic organic solvent may be the same or different from each other.

The reaction of the first invention can be carried out by the method, for example, in which the hydrated metal catalyst (if necessary, it may be previously suspended in water) and the hydrophobic organic solvent are mixed to carry out azeotropic dehydration treatment in the reaction system under reflux, then, pyran-4-one and/or dihydropyran-4-one is/are added thereto, and the mixture is reacted under hydrogen gas atmosphere with stirring, etc. The reaction temperature at that time is preferably 0 to 100° C., further preferably 5 to 60° C., and the reaction pressure is the reaction pressure is preferably 0.1 to 10 MPa, further preferably 0.1 to 1 MPa.

Also, it is preferred that the organic solvent to be used for the dehydration treatment and the hydrophobic organic solvent to be used in the reaction are the same in the point of the preparation method, and depending on the cases, for example, it is also possible to carry out the reaction by subjecting to dehydration treatment with 1,2-dimethoxyethane, etc., and then, the solvent is replaced with toluene, etc.

Incidentally, the final product, tetrahydropyran-4-one is isolated and purified by a general method such as neutralization, extraction, filtration, concentration, distillation, column chromatography, etc., after completion of the reaction.

The above-mentioned pyran-4-one represented by the formula (2') to be used in the first invention can be obtained by the third invention which comprises subjecting 5,5-dialkoxy-3-oxopentanal represented by the formula (3):

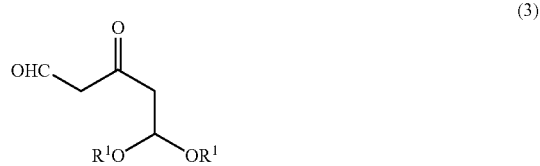

(3)

wherein $R^1$ has the same meaning as defined above, or an equivalent thereof, or a salt thereof to cyclization by reacting an acid.

The 5,5-dialkoxy-3-oxopentanal to be used in the third invention is represented by the above-mentioned formula (3). In the formula (3), $R^1$ is an alkyl group, preferably a straight or branched alkyl group having 1 to 12 carbon atoms, more preferably a straight or branched alkyl group having 1 to 6 carbon atoms, and there may be mentioned, for example, a methyl group, an ethyl group, a propyl group, a butyl group, a pentyl group, a hexyl group, etc. Incidentally, these groups contain various kinds of isomers. Also, two $R^1$s may be bonded to each other to form a ring, and the ring thus formed may be mentioned, for example, 1,3-dioxolane, etc.

Specific examples of the 5,5-dialkoxy-3-oxopentanal may be mentioned, for example, 5,5-dimethoxy-3-oxopentanal, 5,5-diethoxy-3-oxopentanal, 5,5-di-n-propoxy-3-oxopentanal, 5,5-diisopropoxy-3-oxopentanal, 5,5-di-n-butoxy-3-oxopentanal, 5,5-diisobutoxy-3-oxopentanal, 5,5-di-tert-butoxy-3-oxopentanal, etc. Also, specific examples of the equivalent of the 5,5-dialkoxy-3-oxopentanal may be mentioned, for example, 1,1,5,5-tetramethoxypentan-3-one, 1,5-dimethoxy-1,4-pentandien-3-one, 1,1,5-trimethoxypentan-4-en-3-one, etc.

The organic solvent to be used in the cyclization of the third invention is not specifically limited so long as it does not inhibit the reaction, and there may be mentioned, for example, an alcohol such as methanol, ethanol, isopropyl alcohol, t-butyl alcohol, ethylene glycol, triethylene glycol, etc.; a ketone such as acetone, methyl ethyl ketone, methyl isobutyl ketone, etc.; an amide such as N,N-dimethylformamide, N,N-dimethylacetamide, N-methyl-pyrrolidone, etc.; an urea such as N,N'-dimethylimidazolidinone, etc.; a sulfoxide such as dimethylsulfoxide, etc.; a nitrile such as acetonitrile, propionitrile, benzonitrile, etc.; an ether such as diethyl ether, diisopropyl ether, tetrahydrofuran, dioxane, etc.; an aliphatic hydrocarbon such as pentane, hexane, heptane, cyclohexane, etc.; an aromatic hydrocarbon such as benzene, toluene, xylene, etc., preferably a nitrile, a sulfoxide, an amide, an aliphatic hydrocarbon, an aromatic hydrocarbon, further preferably an aromatic hydrocarbon, a nitrile is/are used. Incidentally, these organic solvents may be used alone or in combination of two or more in admixture.

An amount of the above-mentioned organic solvent may be optionally adjusted depending on a degree of uniformity or condition of stirring of the reaction solution, and is preferably 0.5 to 50 g, more preferably 1 to 20 g, further preferably 1 to 10 g based on 1 g of the 1,1-dialkoxybutan-3-one or an equivalent thereof.

As the acid to be used in the cyclization of the third invention, there may be mentioned, for example, a mineral acid such as hydrochloric acid, sulfuric acid, nitric acid, phosphoric acid, etc.; a carboxylic acid such as formic acid, acetic acid, etc.; an organic sulfonic acid such as methanesulfonic acid, trifluoromethanesulfonic acid, etc., preferably a mineral acid, further preferably hydrochloric acid, sulfuric acid is/are used. Incidentally, these acids may be used alone or in combination of two or more in admixture.

An amount of the above-mentioned acid to be used is preferably 1.0 to 20 mol, further preferably 1.1 to 6.0 mol based on 1 mol of the 1,1-dialkoxybutan-3-one or an equivalent thereof.

The cyclization of the third invention may be carried out by a method in which, for example, 1,1-dialkoxybutan-3-one or an equivalent thereof, a formic acid ester, a base and an organic solvent are mixed and reacted preferably at −30 to 150° C., further preferably at −20 to 130° C. with stirring to obtain a salt of 5,5-dialkoxy-3-oxopentanal or a salt of an equivalent thereof, then, an acid is added to the mixture and reacted preferably at −30 to 150° C., more preferably at −20 to 130° C., further preferably at −20 to 100° C., most preferably at −5 to 60° C. with stirring, and the like. Incidentally, the reaction pressure at that time is not particularly limited.

Also, the sodium salt of 5,5-dialkoxy-3-oxopentanal represented by the above-mentioned formula (3) or the salt of the equivalent thereof which is the seventh invention is a novel compound, and specific examples of the sodium salt of 5,5-dialkoxy-3-oxopentanal may be mentioned, for example, sodium salt of 5,5-dimethoxy-3-oxopentanal, sodium salt of 5,5-diethoxy-3-oxopentanal, sodium salt of 5,5-di-n-propoxy-3-oxopentanal, sodium salt of 5,5-diisopropoxy-3-oxopentanal, sodium salt of 5,5-di-n-butoxy-3-oxopentanal, sodium salt of 5,5-diisobutoxy-3-oxopentanal, sodium salt of 5,5-di-tert-butoxy-3-oxopentanal, etc. Also, specific examples of a sodium salt of an equivalent of 5,5-dialkoxy-3-oxopentanal, there may be mentioned, for example, a sodium salt of 1,1,5,5-tetramethoxypentan-3-one, 1,5-dimethoxy-1,4-pentandien-3-one, or 1,1,5-trimethoxypentan-4-en-3-one, etc.

Also, the salt of the 5,5-dialkoxy-3-oxopentanal represented by the above-mentioned formula (3) or the salt of the equivalent thereof can be obtained by the fourth invention which comprises reacting 1,1-dialkoxybutan-3-one represented by the formula (4):

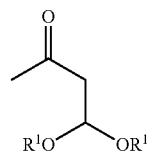

(4)

wherein $R^1$ has the same meaning as defined above, or an equivalent thereof, and a formic acid ester represented by the formula (5):

(5)

wherein $R^2$ represents an alkyl group, in the presence of a base in an organic solvent.

The 1,1-dialkoxybutan-3-one or an equivalent thereof to be used in the reaction of the fourth invention is represented by the above-mentioned formula (4). In the formula (4), $R^1$ has the same meaning as those mentioned in the above-mentioned formula (3).

The formic acid ester to be used in the reaction of the fourth invention is represented by the above-mentioned formula (5). In the formula (5), $R^2$ is an alkyl group, preferably a straight or branched alkyl group having 1 to 12 carbon atoms, more preferably a straight or branched alkyl group having 1 to 6 carbon atoms, and there may be mentioned, for example, a methyl group, an ethyl group, a propyl group, a butyl group, a pentyl group, a hexyl group, etc. Incidentally, these groups contain various kinds of isomers.

An amount of the above-mentioned formic acid ester is preferably 1.0 to 5.0 mol, further preferably 1.1 to 3.0 mol based on 1 mol of the 1,1-dialkoxybutan-3-one or an equivalent thereof.

As the base to be used in the reaction of the fourth invention, there may be mentioned, for example, an alkali metal alkoxide such as sodium methoxide, potassium methoxide, etc.; an alkali metal hydroxide such as sodium hydroxide, potassium hydroxide, etc.; an alkali metal hydride such as sodium hydride, potassium hydride, etc.; an alkaline earth metal hydride such as calcium hydride, etc.; an alkali metal carbonate such as sodium carbonate, potassium carbonate, etc.; an alkali metal hydrogen carbonate such as sodium hydrogen carbonate, potassium hydrogen carbonate, etc., preferably an alkali metal alkoxide, further preferably sodium methoxide, potassium methoxide is/are used. Incidentally, these based may be used alone or in combination of two or more in admixture.

An amount of the above-mentioned base is preferably 1.0 to 5.0 mol, further preferably 1.1 to 3.0 mol based on 1 mol of the 1,1-dialkoxybutan-3-one or an equivalent thereof.

The pyran-4-one represented by the above-mentioned formula (2') can be also obtained by the fifth invention which comprises subjecting 1,1,5,5-tetraalkoxypentan-3-one represented by the formula (6):

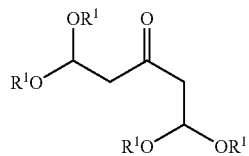

wherein $R^1$ has the same meaning as defined above, or an equivalent thereof to cyclization in the presence of an acid.

The 1,1,5,5-tetraalkoxypentan-3-one or an equivalent thereof to be used in the cyclization of the fifth invention is represented by the above-mentioned formula (6). In the formula (6), $R^1$ has the same meaning as defined above.

As the acid to be used in the cyclization of the fifth invention, there may be mentioned, for example, a mineral acid such as hydrochloric acid, sulfuric acid, nitric acid, phosphoric acid, etc.; a carboxylic acid such as formic acid, acetic acid, etc.; an organic sulfonic acid such as methanesulfonic acid, trifluoromethanesulfonic acid, etc., preferably a mineral acid, further preferably hydrochloric acid, sulfuric acid is/are used. Incidentally, these acids may be used alone or in combination of two or more in admixture.

An amount of the above-mentioned acid to be used is preferably 1.0 to 100 mol, more preferably 1.1 to 10 mol, further preferably 1.1 to 6.0 mol based on 1 mol of the 1,1,5,5-tetraalkoxypentan-3-one or an equivalent thereof.

The cyclization of the fifth invention is carried out in the presence or absence of a solvent. When a solvent is used, it is not particularly limited so long as it does not inhibit the reaction, and there may be mentioned, for example, water; an alcohol such as methanol, ethanol, isopropyl alcohol, t-butyl alcohol, ethylene glycol, triethylene glycol, etc.; a ketone such as acetone, methyl ethyl ketone, methyl isobutyl ketone, etc.; an amide such as N,N-dimethylformamide, N,N-dimethylacetamide, N-methyl-pyrrolidone, etc.; an urea such as N,N'-dimethylimidazolidinone, etc.; a sulfoxide such as dimethylsulfoxide, etc.; a nitrile such as acetonitrile, propionitrile, benzonitrile, etc.; an ether such as diethyl ether, diisopropyl ether, tetrahydrofuran, dioxane, etc.; an aromatic hydrocarbon such as benzene, toluene, xylene, etc. Incidentally, these solvents may be used alone or in combination of two or more in admixture.

An amount of the above-mentioned solvent may be optionally adjusted depending on a degree of uniformity or condition of stirring of the reaction solution, and is preferably 0 to 50 g, further preferably 0 to 10 g based on 1 g of the 1,1,5,5-tetraalkoxypentan-3-one or an equivalent thereof.

The cyclization of the fifth invention can be carried out by a method in which, for example, 1,1,5,5-tetraalkoxypentan-3-one or an equivalent thereof and an acid are mixed and reacted with stirring, and the like. Incidentally, the reaction temperature at that time is preferably at −20 to 100° C., further preferably at −5 to 60° C., and the reaction pressure is not particularly limited.

Incidentally, the obtained pyran-4-one is isolated and purified by a general method such as filtration, neutralization, extraction, concentration, distillation, recrystallization, crystallization, column chromatography, etc., after completion of the reaction.

The sixth invention is a process for preparing dihydropyran-4-one represented by the above-mentioned formula (2"), which comprises reacting pyran-4-one represented by the above-mentioned formula (2') and hydrogen in the presence of a metal catalyst in a mixed solvent of an aprotic solvent and an alcohol solvent.

As the reaction conditions, the same conditions as the reduction of the pyran-4-one represented by the above-mentioned formula (2') may be mentioned.

The second invention of the present invention relates to a process for preparing tetrahydropyran-4-one which carries out the above-mentioned cyclization and reduction continuously.

(A) Cyclization Step

The cyclization step of the present invention is a step in which 1,1-dialkoxybutan-3-one represented by the formula (4) or an equivalent thereof and a formic acid ester represented by the formula (5) are reacted in an organic solvent in the presence of a base to obtain a salt of 5,5-dialkoxy-3-oxopentanal represented by the formula (3) or a salt of an equivalent thereof, and further, an acid is reacted thereto to prepare a crude product containing pyran-4-one represented by the formula (2') as a main component. The cyclization is carried out by the same manner as mentioned above.

Incidentally, according to the cyclization step of the present invention, a crude product containing pyran-4-one as a main component can be obtained, and in the present invention, after completion of the reaction, the reaction solution can be used as such in the next step without effecting isolation and purification of the pyran-4-one, or after subjecting to a treatment such as concentration, etc.

(B) Reduction Step

The reduction step of the present invention is a step of preparing tetrahydropyran-4-one represented by the formula (1) by reacting the crude product containing pyran-4-one represented by the formula (2') as a main component and hydrogen (a) in a mixed solvent of an aprotic solvent and an alcohol solvent, or (b) in the presence of an anhydrous metal catalyst in which a hydrated metal catalyst is subjected to dehydration treatment, in a hydrophobic solvent in the presence of a metal catalyst. The reduction is carried out by the same manner as mentioned above.

An amount of the above-mentioned metal catalyst is preferably 0.00001 to 0.5 mol, further preferably 0.00002 to 0.1 mol based on 1 mol of the 1,1-dialkoxybutan-3-one or an equivalent thereof in terms of the metal atom.

An amount of the hydrogen to be used in the reaction of the present invention is preferably 0.5 to 20 mol, more preferably 1.1 to 10 mol based on 1 mol of the 1,1-dialkoxybutan-3-one or an equivalent thereof.

The reaction conditions of the above-mentioned (a) and (b) are the same as in the first invention.

Also, in the present application, there is provided a process for preparing pyran-4-one which comprises reacting 1,1-dialkoxybutan-3-one or an equivalent thereof represented by the formula (7) and a formic acid ester represented by the formula (5) in an organic solvent in the presence of a base to obtain a salt of 5,5-dialkoxy-3-oxopentanal represented by the formula (3) or a salt of an equivalent thereof, and then, an acid is reacted to the salt to prepare pyran-4-one represented by the formula (2').

The reaction conditions of the above-mentioned process for preparing pyran-4-one are the same as mentioned above.

EXAMPLES

Next, the present invention is explained more specifically by referring to Examples, but the scope of the present invention is not limited by these.

Reference Example 1

Synthesis of 1,1,5,5-tetramethoxypentan-3-one

In a flask made of glass having an inner volume of 500 ml and equipped with a stirring device and a dropping funnel were charged 37 g (0.68 mol) of sodium methoxide and 200 ml of toluene, and while maintaining the liquid temperature to 15° C. or lower, a mixed solution comprising 50 g (0.50 mol) of 1-methoxy-1-buten-3-one and 60 g (1.0 mol) of methyl formate was gently added dropwise to the mixture. After completion of the dropwise addition, the mixture was reacted at 15° C. or lower for 1 hour, and at room temperature for 3 hours. Thereafter, the reaction solution was concentrated under reduced pressure, 50 ml of methanol was added to the concentrate, 60 g (0.6 mol) of 98% sulfuric acid was gently added dropwise to the mixture while maintaining the liquid temperature to 15° C. or lower, and the mixture was reacted under stirring at room temperature for 5 hours. After completion of the reaction, 50% aqueous sodium hydroxide solution was added to the mixture to neutralize the same, the precipitated solid was filtered off, and the obtained filtrate was concentrated. The concentrate was purified by silica gel column chromatography (Eluent; hexane:ethyl acetate=10:1) to give 18.5 g (Isolation yield: 18%) of 1,1,5,5-tetramethoxypentane-3-one as orange liquid.

Physical properties of 1,1,5,5-tetramethoxypentane-3-one were as follows.

CI-MS (m/e); 175 (M-Ome) $^1$H-NMR (CDCl$_3$, δ (ppm)); 2.76 (4H, d, J=5.6 Hz), 3.36 (12H, s), 4.79 (2H, t, J=5.6 Hz)

Example 1

Synthesis of pyran-4-one

In a flask made of glass having an inner volume of 10 ml and equipped with a stirring device and a dropping funnel was charged 1.0 g (4.8 mmol) of 1,1,5,5-tetramethoxypentane-3-one synthesized in the same manner as in Reference example 1, and in an ice bath, 1.2 ml (14.1 mmol) of 12 mol/l hydrochloric acid was gently added dropwise to the material. After completion of the dropwise addition, the mixture was reacted at room temperature for 4 hours. After completion of the reaction, when the reaction solution was analyzed by gas chromatography (Internal standard method), 0.45 g (Reaction yield: 97%) of pyran-4-one was found to be formed.

Example 2

Synthesis of pyran-4-one

In a flask made of glass having an inner volume of 10 ml and equipped with a stirring device and a dropping funnel was charged 1.0 g (4.8 mmol) of 1,1,5,5-tetramethoxypentane-3-one synthesized in the same manner as in Reference example 1, and in an ice bath, 5 ml (130 mmol) of 98% formic acid was gently added dropwise to the material. After completion of the dropwise addition, the mixture was reacted at room temperature for 19 hours. After completion of the reaction, the reaction solution was analyzed by gas chromatography (Internal standard method), 0.45 g (Reaction yield: 97%) of pyran-4-one was found to be formed.

Example 3

Synthesis of pyran-4-one

In a flask made of glass having an inner volume of 1000 ml and equipped with a stirring device, a thermometer and a dropping funnel were charged 81.7 g (1.51 mol) of sodium methoxide and 400 ml of acetonitrile, and in an ice bath, a mixed solution comprising 100 g (0.76 mol) of 1,1-dimethoxybutan-3-one and 68.2 g (1.14 mol) of methyl formate was gently added dropwise to the mixture while maintaining the liquid temperature to 12° C. or lower. After completion of the dropwise addition, the mixture was reacted at 17 to 22° C. for 4 hours to give a reaction mixture containing a sodium salt of 5,5-dimethoxy-3-oxopentanal (containing an equivalent thereof).

Then, in a flask made of glass having an inner volume of 2000 ml and equipped with a stirring device, a thermometer and a dropping funnel was charged 277 ml (3.32 mol) of 12 mol/l hydrochloric acid, and in an ice bath, the above-mentioned reaction mixture containing a sodium salt of 5,5-dimethoxy-3-oxopentanal (containing an equivalent thereof) was gently added dropwise to the mixture while maintaining the liquid temperature to 12° C. or lower. After completion of the dropwise addition, the mixture was reacted at 17 to 22° C. for 16 hours.

After completion of the reaction, while maintaining the liquid temperature to 0° C. or lower, 350 g (1.81 mol) of a methanol solution containing 28% sodium methoxide was gently added dropwise to the mixture to neutralize the same, and after completion of the dropwise addition, the precipitated solid was filtered off. When the filtrate was analyzed by gas chromatography (Internal standard method), 61.9 g (Reaction yield: 83%) of pyran-4-one was found to be formed.

Example 4

Synthesis of Sodium Salt of 5,5-dimethoxy-3-oxopentanal (Including its Equivalent))

In a flask made of glass having an inner volume of 1000 ml and equipped with a stirring device, a thermometer and a dropping funnel were charged 81.7 g (1.51 mol) of sodium methoxide and 400 ml of acetonitrile, and in an ice bath, while maintaining the liquid temperature to 12° C. or lower, a mixed solution comprising 100 g (0.76 mol) of 1,1-dimethoxybutan-3-one and 68.2 g (1.14 mol) of methyl formate was gently added dropwise to the mixture. After completion of the dropwise addition, the mixture was reacted at 17 to 22° C. for 4 hours to give a reaction mixture containing a sodium salt of 5,5-dimethoxy-3-oxopentanal (containing an equivalent thereof). A part of this reaction mixture was filtered, and the obtained solid was dried under reduced pressure to give a sodium salt of 5,5-dimethoxy-3-oxopentanal (containing an equivalent thereof) as a pale yellow solid.

The sodium salt of 5,5-dimethoxy-3-oxopentanal (containing an equivalent thereof) is a novel compound represented by the following physical properties.

FAB-MS; 183 (M) $^1$H-NMR (DMSO-$d_6$, δ (ppm)); 2.61 (1H, brs), 2.86 (1H, brs), 3.41 (6H, s), 4.81 (1H, t, J=5.7 Hz), 5.27 (1H, d, J=10.5 Hz), 9.00 (1H, d, J=10.5 Hz)

Example 5

Synthesis of tetrahydropyran-4-one

In a flask made of glass having an inner volume of 20 ml and equipped with a stirring device, a thermometer, a reflux condenser and a balloon filled with hydrogen were charged 577 mg (6.0 mol) of pyran-4-one, 120 mg (50% wet product; containing 0.03 mmol as a palladium atom) of 5% by weight palladium/carbon, 5 ml of toluene and 1 ml of ethanol, and the mixture was reacted under hydrogen atmosphere at room temperature for 3 hours with stirring. After completion of the reaction, the reaction solution was analyzed by gas chromatography (Internal standard method), 513 mg (Reaction yield: 85.4%) of tetrahydropyran-4-one was found to be formed.

Example 6

Synthesis of tetrahydropyran-4-one

The filtrate obtained in Example 3 was concentrated under reduced pressure, 300 ml of toluene was added to the concentrate, and the mixture was dehydrated by azeotropic distillation (this operation was repeated four times). To the solution were added 500 ml of ethyl acetate and 500 ml of a saturated aqueous sodium chloride solution, and the mixture was stirred. After completion of the stirring, the organic layer and the aqueous layer were separated, the aqueous layer was extracted twice with 500 ml of ethyl acetate, the extracts and the organic layer were combined and the mixture was dried over anhydrous magnesium sulfate. After filtration, the filtrate was concentrated under reduced pressure, and 300 ml of toluene was further added to the concentrate and insoluble materials were filtered off. The filtrate was concentrated again to give 36.1 g of a crude product containing pyran-4-one as a main component as brown liquid.

In a flask made of glass having an inner volume of 20 ml and equipped with a stirring device, a thermometer and a balloon filled with hydrogen were charged 32.3 g of the crude product containing pyran-4-one as a main component, 6.5 g (50% hydrated product; containing 1.5 mmol as a palladium atom) of 5% by weight palladium/carbon, 162 ml of toluene and 24 ml of ethanol, and the mixture was reacted under hydrogen atmosphere at room temperature for 8.5 hours with stirring. After completion of the reaction, the reaction solution was concentrated under reduced pressure, and the concentrate was distilled under reduced pressure (55 to 65° C., 933 Pa) to give 10.18 g (Isolation yield based on 1,1-dimethoxybutan-3-one: 14.9%) of tetrahydropyran-4-one as colorless liquid.

Example 7

Synthesis of dihydropyran-4-one

In a flask made of glass having an inner volume of 20 ml and equipped with a stirring device, a thermometer, a reflux condenser and a balloon filled with hydrogen were charged 3.0 g (31.2 mmol) of pyran-4-one, 0.6 g (50% hydrated product; containing 0.14 mmol as a palladium atom) of 5% by weight palladium/carbon, 30 ml of toluene and 3 ml of ethanol, and the mixture was reacted under hydrogen atmosphere at room temperature for 1 hour. After completion of the reaction, the reaction mixture was filtered, and the filtrate was concentrated. The concentrate was purified by silica gel column chromatography (Eluent; hexane:ethyl acetate=10:1) to give 1.0 g (Isolation yield; 33%) of dihydropyran-4-one as colorless liquid.

Physical properties of dihydropyran-4-one are as follows.

CI-MS (m/e); 99 (M+1) 1H-NMR (CDCl$_3$, δ (ppm)); 2.57 to 2.63 (2H, m), 4.50 (2H, dd, J=7.6 Hz, 6.8 Hz), 5.41 (1H, d, J=6.1 Hz), 7.35 (1H, d, J=6.1 Hz)

Example 8

Synthesis of tetrahydropyran-4-one

In a flask made of glass having an inner volume of 20 ml and equipped with a stirring device, a thermometer, a reflux condenser and a balloon filled with hydrogen were charged 500 mg (5.1 mmol) of dihydropyran-4-one synthesized in Reference example 1, 100 mg (50% hydrated product; containing 0.02 mmol as a palladium atom) of 5% by weight palladium/carbon, 5 ml of toluene and 0.5 ml of ethanol, the mixture was reacted under hydrogen atmosphere at room temperature for 3 hours with stirring. After completion of the reaction, when the reaction solution was analyzed by gas chromatography (Internal standard method), 361 mg (Reaction yield: 71%) of tetrahydropyran-4-one was found to be formed.

Example 9

Synthesis of tetrahydropyran-4-one

In an apparatus made of glass having an inner volume of 50 ml and equipped with a stirring device, a thermometer, a reflux condenser and a Dean-Stark device were charged 0.2 g of 5% by weight palladium/carbon (50% hydrated product) and 30 ml of toluene, and the mixture was refluxed under normal pressure for 30 minutes with stirring (azeotropic dehydration). Then, a balloon filled with hydrogen was equipped to the flask, 1.0 g (10.4 mmol) of pyran-4-one was added to the mixture, and the mixture was reacted under hydrogen atmosphere at room temperature for 12 hours with stirring. After completion of the reaction, when the reaction solution was analyzed by gas chromatography (Internal standard method), 807 mg (Reaction yield: 77%) of tetrahydropyran-4-one was found to be formed.

Example 10

Synthesis of tetrahydropyran-4-one

In an apparatus made of glass having an inner volume of 50 ml and equipped with a stirring device, a thermometer, a reflux condenser and a Dean-Stark device were charged a liquid in which 0.2 g of 5% by weight palladium/carbon (50% hydrated product) had been suspended in 1 ml of water and 30 ml of toluene, and the mixture was refluxed under normal pressure for 60 minutes with stirring (azeotropic dehydration). Then, a balloon filled with hydrogen was equipped to the flask, 1.0 g (10.4 mmol) of pyran-4-one was added to the mixture, and the mixture was reacted under hydrogen atmosphere at room temperature for 12 hours with stirring. After completion of the reaction, when the reaction solution was analyzed by gas chromatography (Internal standard method), 825 mg (Reaction yield: 79%) of tetrahydropyran-4-one was found to be formed.

Comparative Example 1

Synthesis of tetrahydropyran-4-one

In an apparatus made of glass having an inner volume of 50 ml and equipped with a stirring device, a thermometer, a reflux condenser and a balloon filled with hydrogen were charged 0.2 g of 5% by weight palladium/carbon (50% hydrated product), 1.0 g (10.4 mmol) of pyran-4-one and 30 ml of toluene, and the mixture was reacted under hydrogen atmosphere at room temperature for 12 hours with stirring. After completion of the reaction, when the reaction solution was analyzed by gas chromatography (Internal standard method), 86 mg (Reaction yield: 7%) of tetrahydropyran-4-one was found to be formed.

UTILIZABILITY IN INDUSTRY

The present invention relates to a process for preparing tetrahydropyran-4-one from pyran-4-one and/or dihydropyran-4-one, and the tetrahydropyran-4-one is a compound useful for a starting material or a synthetic intermediate of a medicine, agricultural chemicals, etc.

Also, according to the present invention, an industrially suitable process for preparing pyran-4-one which can obtain pyran-4-one from inexpensive starting materials in high yield and by a simple and easy process can be provided.

According to the present invention, an industrially suitable process for preparing tetrahydropyran-4-one which can obtain tetrahydropyran-4-one from pyran-4-one in high yield and by a simple and easy process can be provided.

The invention claimed is:

1. A process for preparing tetrahydropyran-4-one represented by the formula (1):

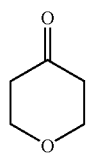

(1)

which comprises reacting at least one kind of dihydropyran-4-one and pyran-4-one represented by the formula (2):

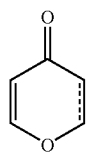

(2)

wherein ----- represents a single bond or a double bond, and hydrogen in the presence of a metal catalyst, in a mixed solvent of an aprotic solvent and an alcohol solvent.

2. The process for preparing tetrahydropyran-4-one according to claim 1, wherein the metal catalyst contains at least one metal atom selected from the group consisting of palladium, platinum and nickel.

3. The process for preparing tetrahydropyran-4-one according to claim 1, wherein the aprotic solvent is an aliphatic hydrocarbon, a halogenated aliphatic hydrocarbon, an aromatic hydrocarbon, a halogenated aromatic hydrocarbon, a carboxylic acid ester, an ether, or a mixture thereof.

4. The process for preparing tetrahydropyran-4-one according to claim 1, wherein an alcohol solvent in the mixed solvent is contained in the range of 5 to 95% by volume.

5. The process for preparing tetrahydropyran-4-one according to claim 1, wherein the compound represented by the formula (2) is pyran-4-one represented by the formula (2'):

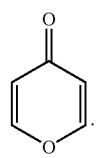

(2')

6. The process for preparing tetrahydropyran-4-one according to claim 5, wherein the pyran-4-one represented by the formula (2') is a compound obtained by reacting 5,5-dialkoxy-3-oxopentanal represented by the formula (3):

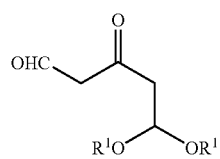

(3)

wherein $R^1$ represents an allkyl group, and two $R^1$s may be bonded to each other to form a ring, or an equivalent thereof, or a salt thereof with an acid.

7. The process for preparing tetrahydropyran-4-one according to claim 6, wherein a salt of the 5,5-dialkoxy-3-oxopentanal represented by the formula (3) or a salt of an equivalent thereof is a compound obtained by reacting 1,1-dialkoxybutan-3-one represented by the formula (4):

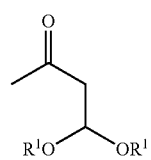

(4)

wherein $R^1$ has the same meaning as defined above, and a formic acid ester represented by the formula (5):

$HCO_2R^2$ (5)

wherein $R^2$ represents an alkyl group, in an organic solvent in the presence of a base.

8. The process for preparing tetrahydropyran-4-one according to claim 5, wherein the pyran-4-one represented by the formula (2') is a compound obtained by subjecting 1,1,5,5-tetraalkoxypentan-3-one represented by the formula (6):

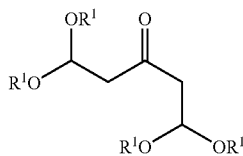

wherein $R^1$ has the same meaning as defined above, or an equivalent thereof to cyclization in the presence of an acid.

9. The process for preparing tetrahydropyran-4-one according to claim 5, wherein the pyran-4-one represented by the formula (2') is a compound obtained by reacting 1,1-dialkoxybutan-3-one represented by the formula (7):

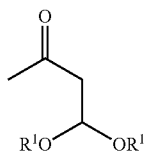

wherein R has the same meaning as defined above, or an equivalent thereof and a formic acid ester represented by the formula (5):

$HCO_2R^2$      (5)

wherein $R^2$ has the same meaning as defined above, in an organic solvent in the presence of a base, to form a salt of 5,5-dialkoxy-3-oxopentanal represented by the formula (3):

(3)

wherein $R^1$ has the same meaning as defined above, or a salt of an equivalent thereof, then, reacting an acid thereto.

10. The process for preparing tetrahydropyran-4-one according to claim 9, wherein the organic solvent is an aromatic hydrocarbon or a nitrile.

11. A process for preparing tetrahydropyran-4-one which comprises two steps of (A) cyclizaion step in which 1,1-dialkoxybutan-3-one represented by the formula (7):

(7)

wherein $R^1$ represents an alkyl group, and two $R^1$s may be bonded to form a ring, and a formic acid ester represented by the formula (5):

$HCO_2R^2$      (5)

wherein $R^2$ represents an alkyl group, are reacted in an organic solvent in the presence of a base, to prepare a salt of 5,5-dialkoxy-3-oxopentanal represented by the formula (3):

(3)

wherein $R^1$ has the same meaning as defined above, or a salt of an equivalent thereof, and reacting the salt with an acid to prepare crude product containing pyran-4-one represented by the formula (2'):

(2')

as a main component, then, (B) reduction step in which the crude product containing the pyran-4-one as a main component and hydrogen are reacted in the presence of a metal catalyst, in a mixed solvent of an aprotic solvent and an alcohol solvent, to prepare tetrahydropyran-4-one represented by the formula (1).

(1)

12. The process for preparing tetrahydropyran-4-one according to claim 11, wherein the metal catalyst contains at least one metal atom selected from the group consisting of palladium, platinum and nickel.

13. The process for preparing tetrahydropyran-4-one according to claim 11, wherein the aprotic solvent is an aliphatic hydrocarbon, a halogenated aliphatic hydrocarbon, an aromatic hydrocarbon, a halogenated aromatic hydrocarbon, a carboxylic acid ester, an ether, or a mixture thereof.

14. The process for preparing tetrahydropyran-4-one according to claim 11, wherein an alcohol solvent in the mixed solvent is contained in the range of 5 to 95% by volume.

15. The process for preparing tetrahydropyran-4-one according to claim 1, wherein the catalyst is at least one selected from the group consisting of palladium/carbon, palladium/barium sulfate, palladium hydroxide/platinum, platinum/carbon, platinum sulfate/carbon, palladium-platinum/carbon, platinum oxide and Raney nickel.

16. The process for preparing tetrahydropyran-4-one according to claim 1, wherein an amount of the catalyst is 0.0001 to 5 mol based on 1 mol of the pyran-4-one or dihydropyran-4-one in terms of a metal atom.

17. The process for preparing tetrahydropyran-4-one according to claim 1, wherein an amount of the catalyst is 0.0001 to 0.1 mol based on 1 mol of the pyran-4-one or dihydropyran-4-one in terms of a metal atom.

18. The process for preparing tetrahydropyran-4-one according to claim 1, wherein an amount of the hydrogen to be used in the reaction is 0.5 to 20 mol based on 1 mol of the pyran-4-one or dihydropyran-4-one.

19. The process for preparing tetrahydropyran-4-one according to claim 1, wherein the solvent contains 1 to 95% by volume of the alcohol solvent.

20. The process for preparing tetrahydropyran-4-one according to claim 1, wherein the solvent contains 5 to 90% by volume of the alcohol solvent.

21. The process for preparing tetrahydropyran-4-one according to claim 1, wherein the reaction is carried out at a reaction temperature of 0 to 100°C. under a reaction pressure of 0.1 to 10 MPa.

22. The process for preparing tetrahydropyran-4-one according to claim 1, wherein the reaction is carried out at a reaction temperature of 0 to 100°C. under a reaction pressure of 0.1 to 1 MPa.

23. The process for preparing tetrahydropyran-4-one according to claim 1, wherein the reaction is carried out at a reaction temperature of 5 to 60°C. under a reaction pressure of 0.1 to 1 MPa.

* * * * *